United States Patent [19]

Kingston et al.

[11] Patent Number: 5,059,699

[45] Date of Patent: Oct. 22, 1991

[54] WATER SOLUBLE DERIVATIVES OF TAXOL

[75] Inventors: David G. I. Kingston; Zhi-Yang Zhao, both of Blacksburg, Va.

[73] Assignee: Virginia Tech Intellectual Properties, Inc., Blacksburg, Va.

[21] Appl. No.: 573,731

[22] Filed: Aug. 28, 1990

[51] Int. Cl.$^5$ .................. C07D 305/14; A61K 31/335
[52] U.S. Cl. ...................................... 549/511; 514/449
[58] Field of Search .......................................... 549/511

[56] References Cited

U.S. PATENT DOCUMENTS 4,942,184  7/1990  Haugwitz et al. .................. 514/449

OTHER PUBLICATIONS

Wani et al., *J. Am. Chem. Soc.*, 1971, 93, 2325.
McGuire et al., *Ann. Int. Med.*, 1989, 111, 273–279.
Magri et al., *J. Nat. Prod.*, vol. 51, No. 2, 298–306, Mar.–Apr. 1988.
Duetsch et al., *J. Med. Chem.*, 1989, 32, 788–792.

*Primary Examiner*—Mary C. Lee
*Assistant Examiner*—Joseph K. McKane
*Attorney, Agent, or Firm*—Mason, Fenwick & Lawrence

[57] ABSTRACT

Sulfonated 2'-acryloyltaxol and sulfonated 2'-O-acyl acid taxol derivatives are synthesized which have improved water solubility and stability while maintaining bio-activity. In particular, 2'-[(3-sulfo-1-oxopropyl)oxy]taxol sodium salt is synthesized by reacting taxol with acrylic acid, and subsequently reacting the 2'-acryloyltaxol with bisulfite in a Michael reaction. 2'-{[4-((2-sulfoethyl)amino)-1,4-dioxobutyl]oxy}taxol sodium salt and 2'-{[4-((3-sulfopropyl)amino-1,4-dioxobutyl]oxy} taxol sodium salt are synthesized by reacting 2'-succinyltaxol with the tetrabutylammonium salts of taurine and 3-aminopropyl sulfonic acid, respectively, and subsequently exchanging the ammonium with sodium. Glycol derivatives of 2'-O-acyl acid taxols with improved water solubility are synthesized by reaction of a glycol with 2'-O-acyl acid taxol.

8 Claims, 1 Drawing Sheet

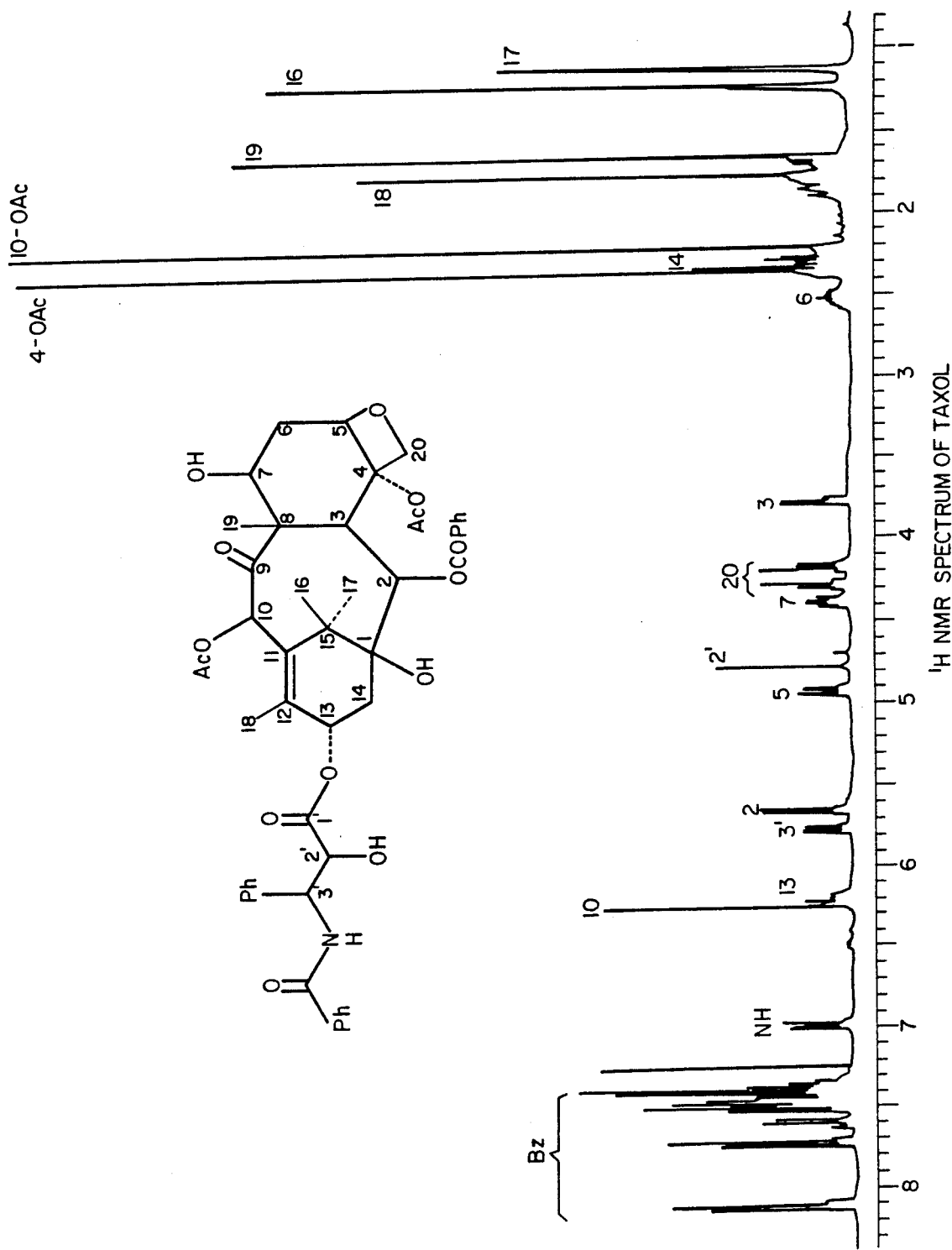

WATER SOLUBLE DERIVATIVES OF TAXOL

FIELD OF THE INVENTION

The present invention relates to water soluble derivatives of taxol with anti-neoplastic activity, and relates more particularly to sulfonated 2'-acryloyltaxol derivatives, 2'-sulfoalkylamino-O-acyl acid taxol derivatives, and 2'-ethylene glycol-O-acyl acid taxol derivatives.

BACKGROUND OF THE INVENTION

Taxol is a naturally occurring diterpenoid which has great potential as an anti-cancer drug, and which has shown activity in several tumor systems. Taxol was first isolated and its structure reported by Wani, et al., in "Plant Anti-Tumor Agents. VI. The Isolation and Structure Of Taxol, A Novel Anti-Leukemic And Anti-Tumor Agent From *Taxus brevifolia*, "*J. Am. Chem. Soc.*, 1971, 93, 2325. Taxol is found in the stem bark of the Western Yew, *Taxus brevifolia*, as well as in *T. baccata* and *T. cuspidata*.

The biological activity of taxol is related to its effect on cell division. Taxol promotes formation of microtubules that form the mitotic spindle during cell division. However, taxol prevents depolymerization of the tubulin forming the microtubules of the mitotic spindle, which is essential for cell division to take place. Thus, taxol causes cell division to stop. Taxol's mechanism is unique since it promotes the formation of tubulin polymers, whereas other anti-cancer drugs, such as vinblastine and colchicine, prevent microtubule formation.

Extensive testing of taxol has not been performed because taxol is in short supply and has not yet been successfully synthesized. Preliminary studies have shown that taxol may have marginal activity in acute leukemia and melanoma, and some activity has been noted in other tumors. Further, studies by McGuire et al. found taxol to be an active agent against drug-refractory ovarian cancer. See "Taxol: A Unique Antineoplastic Agent With Significant Activity In Advanced Ovarian Epithelial Neoplasms," *Ann. Int. Med.*, 1989, 111, 273–279, herein incorporated by reference. However, due to the low water solubility of taxol, doses had to be delivered as infusions diluted in aqueous dextrose solutions.

It should be noted that in phase 1 clinical trials, taxol itself did not show excessive toxic effects, but severe allergic reactions were caused by the emulsifiers administered in conjunction with taxol to compensate for taxol's low water solubility. In fact, at least one patient's death was caused by an allergic reaction induced by the emulsifiers. Therefore, researchers have attempted to create water soluble derivatives of taxol which retain their anti-neoplastic and anti-cancer activity.

With reference to FIG. 1, the structure of taxol is illustrated along with a $^1$H nuclear magnetic resonance (NMR) spectrum of a taxol sample. The NMR signals are well separated and cover the region from 1.0 to 8.2 ppm. For simplicity, the spectrum is divided into three regions: a first region between 1.0 and 2.5 ppm formed by strong 3-proton signals of the methyl and acetate groups as well as complex multiplets caused by certain methylene groups; a second region between 2.5 and 7.0 ppm represents the signals observed from most of the protons on the taxane skeleton and the side chain; a third region between 7.0 and 8.2 ppm is formed by the signals from the aromatic protons of the C-2 benzoate, C-3' phenyl and C-3' benzamide groups. The peaks of the NMR spectrum in FIG. 1 are labeled according to the number of the carbon in the taxol structure to which the protons including the signals are attached.

Magri and Kingston reported on the biological activity of taxols substituted at the C-2' and C-7 positions in order to make them more water soluble. See "Modified Taxols, 4.[1] Synthesis And Biological Activity Of Taxols Modified In The Side Chain," *Journal of Natural Products* vol. 51, no. 2 pp. 298–306, March–April 1988, herein incorporated by reference. A 2'-(t-butyldimethylsilyl)taxol was synthesized and found to be essentially inactive; this was taken as an indication of the need for a free hydroxyl group at the 2' position of the taxol side chain for biological activity. Further, acyl substituents at the 2' position in 2'-acetyltaxol and 2',7-diacetyltaxol were readily hydrolyzed under in vivo conditions, and both showed activity in a cell culture bioassay. The lability of the acyl substituents at the 2' position suggested that 2'-acetyltaxols could serve as pro-drug forms of taxol. (Generally, a prodrug is a compound which exhibits pharmacologic activity after biotransformation.)

Magri and Kingston reported that two taxols with increased water solubility were prepared, 2'-(β-alanyl)-taxol:

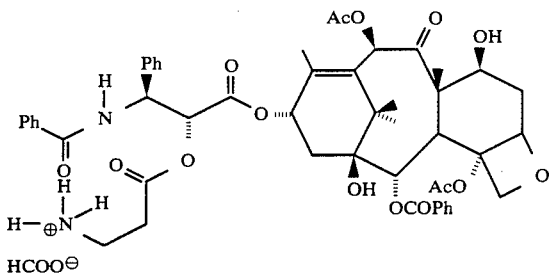

and 2'-succinyltaxol:

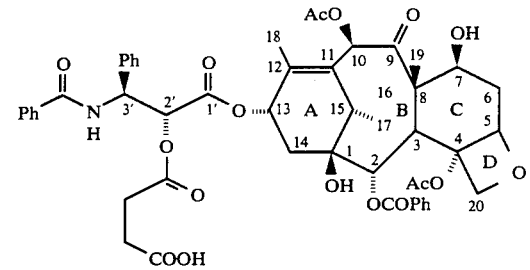

The 2'-(β-alanyl)taxol was found to be active in vivo and in vitro, but was unstable. The 2'-succinyltaxol, prepared by the treatment of taxol with succinic anhydride, had a much diminished P-388 in vivo activity as compared with taxol. Thus, research efforts were concentrated on other derivatives of taxol which did not suffer from instability, or inactivity in vivo or in vitro.

Deutsch et al., in "Synthesis Of Congeners And Prodrugs. 3.[1] Water-Soluble Prodrugs Of Taxol With Potent Antitumor Activity," *J. Med. Chem.* 1989, 32 788–792, herein incorporated by reference, reported that salts of 2'-succinyltaxol and 2'-glutaryltaxol had improved antitumor activities when compared to the free acids. Since these researchers believed that salts prepared with different counterions often have substantially different properties, a variety of 2' substituted taxol salts were synthesized and tested. Triethanolamine and N-methylglucamine salts of the 2' substituted taxol derivatives showed greatly improved aqueous solubility and had more activity than sodium salts. Further, a series of 2'-glutaryltaxol salts were found to have higher activity than their 2'-succinyltaxol analogs. In particular, the taxol salt resulting from the coupling of 2'-glutaryltaxol with 3-(dimethylamino)-1-propylamine using N,N'-carbonyldiimidazole (CDI), demonstrated good solubility and bioactivity.

In addition to increasing the solubility and bioactivity of taxol, it is desirable that the taxol derivatives formed have increased stability to prolong their shelf life. It is believed that salts of taxol esters are very susceptible to base hydrolysis, and water-solubilizing groups, such as carboxylate salts or amine salts, tend to be basic. Thus, it is desired that neutral, water-soluble taxol derivatives be synthesized which also have improved or the equivalent activity to taxol. Organic sulfonate salts tend to be neutral or only slightly basic, and therefore, sulfonate salts of taxol esters should have improved stability. Further, due to the difficulties involved in synthesizing carboxylic and amine salts of taxol esters, it is desirable to find less expensive water-soluble taxol derivatives and processes for forming them.

SUMMARY OF THE INVENTION

The present invention relates to the production of water soluble taxol derivatives, and water soluble sulfonate salts of taxol. In a preferred embodiment, 2'-[(3-sulfo-1-oxopropyl)-oxy] taxol sodium salt is formed by reacting taxol with acrylic acid to form 2'-acryloyltaxol; the 2'-acryloyltaxol is then subjected to a Michael reaction with sodium bisulfite to form the 2'-sulfoethyl ester salt of taxol. In another preferred embodiment, 2'-O-acyl acid taxols, such as 2'-succinyltaxol and 2'-glutaryltaxol, are subjected to a novel reaction with the tetrabutylammonium salt of taurine to form sulfoalkylamine salts of the 2'-O-acyl acid taxols. Another preferred embodiment involves the reaction of amino sulfonic acid salts with succinic or glutaric anhydride, and reaction of the product with taxol to form sulfoalkylamine 2'-O-acyl acid taxol derivatives. In a further embodiment, ethylene glycol derivatives of 2'-O-acyl acid taxols are formed. These compounds exhibit high water solubility, and demonstrate anti-leukemic, antineoplastic, and/or anti-cancer activity.

Thus, it is a primary object of this invention to produce water-soluble derivatives of taxol with high bioactivity and stability.

It is a further object of the present invention to provide a simple and inexpensive process for forming 2'-acryloyltaxols and their sulfonate salt derivatives.

It is yet another object of the present invention to produce 2'-O-acyl acid taxols and their sulfoalkylamine salts.

It is a still further object of the present invention to produce sulfoalkylamine derivatives of 2'-O-acyl acid taxols by simple and inexpensive processes.

It is yet a further object of the present invention to produce hydroxyalkoxy derivatives of 2'-O-acyl acid taxol.

DESCRIPTION OF THE DRAWINGS

FIG. 1 is a representation of the taxol structure and its nuclear magnetic resonance spectrum with peaks labeled according to the part of the taxol structure to which they correspond.

DETAILED DESCRIPTION OF THE INVENTION

Taxol was obtained from the National Cancer Institute. $^1$H-NMR and $^{13}$C-NMR spectra were made with a Bruker 270SY 270 MHz spectrometer; 2D-NMR were obtained using a Bruker WP200 200 MHz spectrometer. Chemical shifts are all recorded in parts per million (ppm) downfield from TMS in $^1$H-NMR, and $^{13}$C-NMR chemical shifts are based on chloroform's shift at 77.0 pm or on the TMS shift at 0 ppm. Samples were generally recorded while in CDCl$_3$ or CD$_3$OD at ambient temperature. Mass spectra were obtained using a Finnegan-MAT 112 gas chromatograph-mass spectrometer and VG 7070 HF mass spectrometer equipped with data system, FAB source, and EI/CI source. NMR and mass spectroscopy data are most useful in studying taxol and its derivatives, with other methods, such as IR and UV, providing additional structure confirmation information.

Other analytical instruments used included Perkin-Elmer 710B infrared and Perkin-Elmer 330 UV-visible spectrophotometers, and a Perkin-Elmer polarimeter. HPLC was carried out on an apparatus consisting of a Waters M6000 pump, a Rheodyne injection valve, a Waters Radial-Pak RLM-100 RP-8 column, and a Waters 440 UV detector.

2'-ACRYLOYLTAXOLS

2'-[(3-sulfo-1-oxopropyl)oxy]taxol sodium salt was prepared by coupling taxol with acrylic acid followed by Michael addition of bisulfite ion. Taxol was reacted with the acrylic acid using isobutylchloroformate as the coupling agent. This produced 2'-acryloyltaxol in 94% yield after purification via flash chromatography (silica gel, 1/1 dichloromethane/ethyl acetate). Using TLC, the coupling of acrylic acid to taxol was found to be 90% complete in 15 hours at 60° C. The disubstituted C-2', C-7 product was not formed after extended reaction times. Proton NMR spectra of the 2'-acryloyltaxol showed that the signal for the C-2'proton was shifted downfield to 5.46 ppm (d, j=3), from the 4.73 ppm shift for the C-2'proton in unsubstituted taxol. The downfield shift is consistent with acylation of the C-2'-hydroxyl group. Since the signal for the C-7 proton at 4.43 ppm was essentially unchanged when compared with the unsubstituted taxol C-7 proton signal at 4.38 ppm, it was concluded that no reaction had taken place at the C-7 position. Mass spectroscopy indicated a molecular weight of 907 with peaks at m/z 930 (MNa$^+$) and 908 (MH$^{30}$).

The 2'-acryloyltaxol was then reacted with sodium bisulfite in a Michael addition reaction. Sodium bisulfite was used because it is a good nucleophile, and because it provides suitable pH conditions for the reaction. Proton NMR spectra of the Michael addition reaction product were contrasted with the spectra of the 2'-acryloyltaxol. The signals in the NMR spectra of the 2'-acryloyltaxol that are due to the presence of the vinyl protons were not present in the spectra of the Michael addition product. However, two triplets at 3.14 ppm and 2.93 ppm indicated the presence of the two new methylene groups in the Michael addition product. Mass spectroscopy of the Michael reaction product indicated a molecular weight of 1011 with peaks present at m/z 1034 (MNa$^+$) and 1012 (MH$^+$).

The formation of 2'-[(3-sulfo-1-oxopropyl)oxy]taxol sodium salt was attempted in a one-step reaction by combining taxol with 3-hydroxy-3-oxopropyl sulfonic acid in the presence of pyridine and DCC (dicyclohexylcarbodiimide), but no product was obtained. This is possibly due to inter-molecular attack by the sulfonyl group on the reaction intermediate.

2'-O-ACYL ACID TAXOL DERIVATIVES

2'-{[4-((2-sulfoethyl)amino)-1,4-dioxobutyl]oxy}taxol sodium salt and 2'-{[4-((3-sulfopropyl)amino-1,4-dioxobutyl]-oxy}taxol sodium salt were produced in high yield by coupling 2'-succinyltaxol with taurine (2-aminoethyl sulfonic acid) and 3-aminopropyl sulfonic acid tetrabutylammonium salts, respectively. Note that other quaternary ammonium salts may be used to make the aminoalkyl sulfonic acids organic solvent soluble. 2'-succinyltaxol was formed by the reaction of succinic anhydride with taxol for two hours at room temperature in pyridine or DMP. In comparison with the NMR spectrum of taxol, the NMR spectrum of 2'-succinyltaxol showed a downfield shift of the C-2' proton signal to 5.51 ppm, and the succinyl proton caused multiplets centered about 2.6 ppm.

The 2'-succinyltaxol was then reacted with taurine tetrabutylammonium salt using isobutylchloroformate as the coupling agent. 2'-{[4-((2-sulfoethyl)amino)-1,4-dioxobutyl]-oxy}taxol tetrabutylammonium salt was produced in 100% yield after isolation via flash chromatography on silica gel using 7/1 dichloromethane/methanol. The reaction was only 80% complete in two hours as monitored by TLC; in order to obtain 100% yield, extended reaction times were necessary. The NMR spectrum of the sulfoalkylamine derivative of 2'-succinyltaxol showed new peaks at 3.6 ppm and 2.94 ppm for the two methylene groups. The sodium salt of 2'-{[4-((2-sulfoethyl)amino)-1,4-dioxobutyl]oxy}taxol was achieved by running 2'-{[4-((2-sulfoethyl)amino-1,4-dioxo-butyl]oxy}taxol tetrabutylammonium salt through a Dowex 50 ion exchange column (Na+ form). An NMR spectrum of the sodium salt showed the absence of signals for the tetrabutyl group. Mass spectroscopy of the sodium salt indicated a molecular weight of 1082 by the presence of peaks at m/z 1105 (MNa+) and 1083 (MH+). 2'-{[4-((3-sulfopropyl)amino)-1,4-dioxobutyl]oxy}taxol sodium salt was prepared by the same method used for the sulfoethylaminotaxol sodium salt; however, the taurine was replaced with 3-amino-1-sulfopropionic acid tetrabutylammonium salt. An NMR spectrum confirmed the synthesis of the 3-sulfopropylamino derivative; new peaks were present at 3.28, 1.98, and 2.87 ppm, representing the three additional methylene groups forming the propyl moiety. The sodium salt form of the sulfopropylamino-succinyltaxol derivative was formed by passing the tetrabutylammonium salt through a Dowex 50 ion exchange column (Na+ form). Mass spectroscopy of the sodium salt of the sulfopropylaminosuccinyltaxol derivative indicated a molecular weight of 1096 by the presence of peaks at m/z 1119 (MNa+) and 1097 (MH+).

It is also contemplated that an amide linkage can be formed between an amino sulfonic acid and an anhydride or diacid, and that the product can be reacted with taxol to form water soluble 2'-O-acyl acid taxol derivatives. Preferably, the amino sulfonic acid is an organic solvent soluble salt.

Attempts to form 2'-}[4-((2-sulfoethyl)amino-1,4-dioxobutyl]oxy}taxol sodium salt directly from 2'-succinyltaxol in a one-step reaction were unsuccessful. 2'-succinyltaxol was combined with triethanolamine, isobutylchloroformate, tetrahydrofuran (THF), taurine, DMF, and water. However, water, necessary to solubilize taurine, hydrolyzed the mixed anhydride intermediate back to the starting material. When nonaqueous conditions were tried, the reaction still did not succeed because the taurine did not dissolve in the organic solvents.

2'-{[4-((2-ethanethiol)amino)-1,4-dioxobutyl]oxy} taxol was prepared in low yield by combining 2'-succinyltaxol with triethylamine, isobutylchloroformate, THF, 2-thioethylamine and dichloromethane. Attempts to oxidize the thiol to the desired sulfonic acid with meta-chloroperbenzoic acid, MCPBA, and dichloromethane did not yield appreciable amounts of the desired sulfoalkylamine succinyltaxol derivative.

ETHYLENE GLYCOL DERIVATIVES OF SUCCINYLTAXOL

2'-{[4-((hydroxylethyl)oxy)-1,4-dioxobutyl]oxy}taxol was prepared by coupling succinyltaxol with ethylene glycol. The hydroxyethyloxysuccinyltaxol derivative was formed in 83% yield after a reaction time of 20 hours at room temperature. The hydroxyethyloxysuccinyltaxol derivative was made in order to convert the secondary hydroxyl group at the 2' position in taxol to a primary hydroxyl group; it is hypothesized that the hydroxyl group in the product is more reactive than that of the hydroxyl in taxol, and that this will make it possible to make other taxol derivatives under mild conditions. An NMR spectrum of the ethylene glycol derivative showed the presence of new peaks at 3.7 ppm and 4.1 ppm, which are assigned to the two new methylene groups of the hydroxyethyloxy derivative. Mass spectroscopy indicated a molecular weight of 997 by the presence of peaks at m/z 1020 (MNa+) and 998 (MH+).

2'-γ-AMINOBUTYRYLTAXOL FORMATE

2'-γ-aminobutyryltaxol formate was synthesized by coupling taxol with N-carbobenzyloxy(CBZ)-γ-aminobutyric acid followed by deprotection of the amine. Taxol was reacted with N-CBZ-γ-aminobutyric acid using dicyclohexylcarbodiimide (DCC) as the coupling agent. The resulting 2'-NCBZ-γ-aminobutyryl taxol was produced in 75% yield after purification via preparative TLC with silica gel and 3/2 hexane/ethyl acetate. DCC decomposes to dicyclohexylurea with the addition of water, so the excess reagents used to drive the reaction did not present a problem; most of the dicyclohexylurea and N-CBZ-γ-aminobutyric acid were removed by filtration. Deprotection of the 2'-N-CBZ-γ-aminobutyryltaxol was effected using 5% Pd/C as a catalyst and formic acid as a hydrogen source. Formic acid provides an active form of hydrogen for removal of CBZ protecting groups, and the reaction yields the 2'-γ-aminobutyryltaxol derivative as a formate salt, which is more water soluble than the neutral form. NMR confirmed the synthesis of the 2'-γ-aminobutyryl taxol formate. However, the compound was unstable in methanol solution and decomposed back to taxol after a few hours. This instability precluded further consideration of 2'-γ-aminobutyryltaxol formate as a prodrug form of taxol.

WATER SOLUBILITY

Water solubilities for all compounds were determined by the partition coefficient between 1-octanol and water. Octanol saturated with distilled water and distilled water saturated with octanol were used for the solubility determinations. Partition experiment results showed that 2'-[(3-sulfo-1-oxopropyl)oxy]taxol sodium salt is 210 times more water soluble than taxol, 2'-{[4-((2-sulfoethyl)amino)-1,4-dioxobutyl]oxy}taxol sodium salt is 191 times more soluble than taxol, and 2'-{[4-((3-sulfopropyl)amino)-1,4-dioxobutyl]oxy}taxol sodium salt is 118 times more water soluble than taxol.

EXAMPLES

The following nonlimiting examples provide specific synthesis methods for preparing the water soluble taxol derivatives of the present invention. All technical and scientific terms used herein have the same meaning as commonly understood by one of ordinary skill in the art. Other methods and materials similar or equivalent to those described herein can be used in the practice or testing of the present invention.

EXAMPLE 1

Triethylamine, 50 µl and acrylic acid 30 µl were dissolved in 5 ml dry THF in a 25 ml round-bottom flask under an argon gas atmosphere. After cooling the solution to 0° C. in an icebath, 50 µl of isobutylchloroformate were added, and the reaction mixture was warmed to room temperature over a 15-minute period. One hundred milligrams of taxol were added to the reaction mixture, and the solution was stirred at 60° C. for 15 hours, and monitored by TLC with dichloromethane/ethyl acetate (2/1). Triethylamine hydrochloride precipitated during the reaction, and was removed by filtration. The solvent was then removed in vacuo, and the product was purified via flash chromatography using silica gel and 1/1 dichloromethane/ethyl acetate. This yielded 100 mg (94%) of 2'-acryloyltaxol:

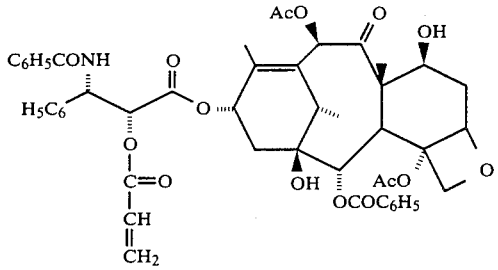

The acryloyl moiety on the 2'-acryloyltaxol is a good Michael acceptor due to the electrophilic β alkene carbon atom which is subject to nucleophilic attack. Thus reaction of 2'-acryloyltaxol with suitable nucleophiles will result in Michael addition at the 2' position. An 85 mg quantity of the 2'-acryloyltaxol was dissolved in about 3 ml of distilled isopropanol, and 84 mg of sodium meta-bisulfite were dissolved in about 1 ml of distilled water. The two solutions were mixed together, and the reaction mixture stirred at 60° C. for about 15 hours. TLC with 10/1 dichloromethane/methanol was used to monitor the reaction. The solvents were then removed under vacuum, and water was removed by azeotroping with acetonitrile. Flash chromatography with 2/1 dichloromethane/isopropanol was used to purify the product. A yield of 83.5 mg (83.5%) of 2'-[(3-sulfo-1-oxopropyl)oxy]taxol sodium salt resulted:

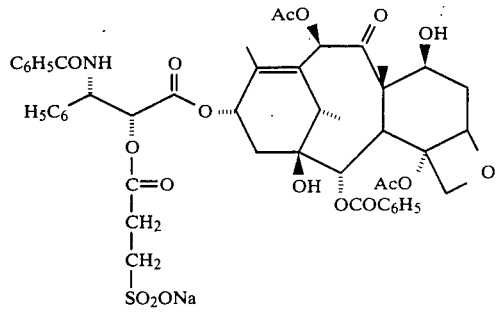

NMR, MS, UV, and IR (KBr) were performed on samples of the product, and optical rotation, and melting point were determined, with the characterization data and NMR data presented in Tables 1 and 2 below.

TABLE 1

Characterization Data For
2'-[(3-sulfo-1-oxopropyl)oxy]taxol sodium salt

| | |
|---|---|
| m.p. | 175–176° C. |
| $[\alpha]_D^{20}$ | −30° (0.0012, MeOH) |
| IR (KBr): | 3500, 2950, 1760, 1730, 1660, 1380, 1250, 1190, 1100, 800 cm$^{-1}$ |
| UV $\lambda$MeOH max: | 279 nm ($\epsilon$ 579), 270 nm ($\epsilon$ 869), 228 nm ($\epsilon$ 15072) |
| MS (FAB): | 1034 (MNa$^+$), 1012 (MH$^+$) |

TABLE 2

NMR Data For
2'-[(3-sulfo-1-oxopropyl)oxy]taxol sodium salt

| Position | $^1$H Shift (ppm from TMS) Coupling (hertz) | $^{13}$C Shift (ppm from TMS) |
|---|---|---|
| C-1 | | * |
| C-2 | 6.2 (d,7) | 75 |
| C-3 | 3.82 (d,7) | 45.8 |
| C-4 | | 80.5 |
| C-5 | 5.0 (d,9) | 84 |
| C-6 | 2.48 m | 35.2 |
| C-7 | 4.35 m | 76 |
| C-8 | | 57.9 |
| C-9 | | 203.8 |
| C-10 | 6.45 s | 70.8 |
| C-11 | | 131 |
| C-12 | | 141 |
| C-13 | 6.09 (t,8) | 75.4 |
| C-14 | 2.48 m | 35.8 |
| C-15 | | 43 |
| C-16 | 1.15 s | 25.9 |
| C-17 | 1.17 s | 19.8 |
| C-18 | 1.95 s | 13.8 |
| C-19 | 1.67 s | 9.4 |
| C-20 | 4.21 s | 70.8 |
| C-1' | | 171 |
| C-2' | 5.45 (d,3) | 74 |
| C-3' | 5.84 (d,7) | 53.1 |
| N—H | 7.26 (t,9) | |
| CH$_3$(OAc) | 2.2 s | 21 |
| CH$_3$(OAc) | 2.4 s | 21.9 |
| Bz | 7.4–8.1 m | 126.8–138.1 |
| CO(OAc) | | 168.4 |
| CO(OAc) | | 169.9 |
| CO(OBz) | | 166.2 |
| CO(NBz) | | 168.2 |
| C-1" | | 170.2 |
| C-2" | 2.93 (t 8) | 29.2 |
| C-3" | 3.14 (t 8) | 63.2 |

* under CHCl$_3$ signal

Note that it is anticipated that the acrylic acid used may be replaced with other members of the acrylic acid family which are also good Michael acceptors, and that the salt-forming moiety may be another alkaline metal, or an ammonio group, such as a tetrabutylammonium group. It is also envisioned that the salt forming moiety may be replaced with H. Biological testing of 2'-](3-sulfo-1-oxopropyl)oxy]taxol sodium salt demonstrated that the compound is bioactive in addition to having improved water solubility.

EXAMPLE 2

A 206 mg quantity of taxol was combined with 2.9 mg of 4-dimethylaminopyridine (DMAP) and 49 mg of succinic anhydride in a 25 ml flask equipped with a magnetic stirrer. A 2.0 ml quantity of dry pyridine was added, and the solution was stirred at room temperature for 2.5 hours. Several milliters of water were then added to produce a white precipitate in an opaque suspension. Several milliters of dichloromethane were then added to extract the products. Addition of 1 ml of concentrated HCl caused the white aqueous suspension to disappear. Sodium sulphate was used to dry the dichloromethane layer, which was then filtered and evaporated. TLC with 7/1 $CH_2Cl_2MeOH$ indicated only a trace of pyridine remaining. The remaining pyridine was removed by the cyclical addition of heptane followed by evaporation; this yield 218 mg of succinyl-taxol, representing a 96.6% yield. Proton NMR of the product matched values given in the literature. The structure was also confirmed using 2D-NMR HOMO COSY (homonuclear correlation spectroscopy).

Taurine, $H_2NCH_2CH_2SO_3H$, is a highly polar compound which is essentially insoluble in organic solvents such as chloroform. Taurine derivatives of organic acids have been made in the past by treating the acid chloride with taurine under Schotten-Baumann conditions (i.e., in basic aqueous or aqueous-ethanolic solution). This method was unacceptable for taxol because it is readily hydrolyzed in base, and would thus decompose under the reaction conditions. In order to overcome this problem, a new method was developed which involved the addition of taurine to tetrabutylammonium hydroxide, followed by removal of unreacted materials and evaporation. This yielded the tetrabutylammonium salt of taurine instead of the sodium salt used in the prior art. The tetrabutylammonium salt of taurine is soluble in organic solvents, such as dichloromethane. Thus, 2'-succinyltaxol in THF and triethylamine can be reacted with isobutylchloroformate and taurine tetrabutylammonium salt to form the tetrabutylammonium salt of the taxol taurine derivative. Note that the intermediate is a mixed anhydride, which hydrolyzes back to the starting compound in the presence of water.

A minimum volume of distilled water was used to dissolve 250 mg taurine in a flask, and 1 ml of aqueous tetrabutylammonium hydroxide was added to the solution. The solution was stirred at room temperature for one hour, and then evaporated to dryness. The dry product was dissolved in dry THF (about 15 ml), filtered, and the filtrate was evaporated until dry. The dried product was then redissolved in 2 ml of dried THF.

PREPARATION OF 2'-{[4-((2-SULFOETHYL)AMINO)-1,4-DIOXOBUTYL]OXY}TAXOL TETRABUTYLAMMONIUM SALT

A solution of 2'-succinyltaxol, formed by dissolving 122 mg of 2'-succinyltaxol in about 4 ml of dried THF and 50 μl of triethylamine, was cooled to about 0° C. The solution was then combined with 50 μl of isobutylchloroformate, the reaction mixture was warmed to room temperature over a 15-minute period, and 0.5 ml of taurine tetrabutylammonium salt in THF solution (equivalent to 91 mg of taurine tetrabutylammonium salt) were added. Following the addition of the taurine tetrabutylammonium salt, the reaction mixture was stirred at room temperature for 5 hours, and the reaction was monitored by TLC with 2/1 EtOAc/MeOH. The reaction mixture was then filtered, and the solvents were evaporated. Purification by flash chromatography using silica gel (300×15 mm bed, 7/1 $CH_2Cl_2$/MeOH) yielded 168 mg (100%) of 2'-{[4-((2-sulfoethyl)-amino)-1,4-dioxobutyl]oxy}taxol tetrabutylammonium salt.

The tetrabutylammonium salt was converted to the sodium salt by placing 160 mg of the tetrabutylammonium salt in a beaker with Dowex 50 ion exchange resin in the Na+form (about 3 ml of resin in 3 ml of deionized water). After stirring the mixture at room temperature for 1.5 hours, the mixture was then passed through a small resin column which contained 2 ml of resin in the Na+ form, using deionized water as the solvent.

The solution was azeotroped with acetonitrile to yield 122 mg (91.7% of 2'-{[4-((2-sulfoethyl)amino)-1,4-dioxobutyl]oxy}taxol sodium salt:

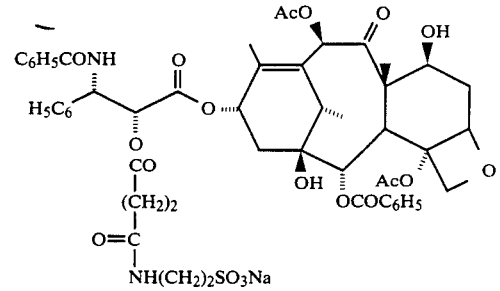

Characterization data are presented below in Table 3, and NMR chemical shift data are presented in Table 4 below.

TABLE 3

| Characterization Data For 2'-{[4-((2-Sulfoethyl)Amino)-1, 4-Dioxobutyl]Oxy}taxol Sodium Salt | |
|---|---|
| m.p. | 174–175° C. |
| $[\alpha]_D^{20}$ | −29.8° (0.0055, MeOH) |
| IR (KBr): | 3450, 3000, 1760, 1730, 1660, 1560, 1400, 1260, 1190, 1050 cm$^{-1}$ |
| UV $\lambda^{MeOH\ max}$: | 279 nm (ε 649), 271 nm (ε 8920), 228 nm (ε 12824) |
| MS (FAB): | 1105 (MNa+), 1083 (MH+) |

TABLE 4

| | NMR Data For 2'-((4-((2-Sulfoethyl)Amino)-1, 4-Dioxobutyl)Oxy)taxol Sodium Salt | |
|---|---|---|
| Position | $^1H$ Shift (ppm from TMS) Coupling (hertz) | $^{13}C$ Shift (ppm from TMS) |
| C-1 | | 79 |
| C-2 | 5.66 (d,7) | 76.6 |
| C-3 | 3.8 (d,7) | 47.2 |
| C-4 | | 81.6 |
| C-5 | 5.02 (d,9) | 85.4 |
| C-6 | 2.52 m | 36 |
| C-7 | 4.35 m | 77.3 |

TABLE 4-continued

NMR Data For
2'-((4-((2-Sulfoethyl)Amino)-1,
4-Dioxobutyl)Oxy)taxol Sodium Salt

| Position | $^1$H Shift (ppm from TMS) Coupling (hertz) | $^{13}$C Shift (ppm from TMS) |
|---|---|---|
| C-8 | | 58.8 |
| C-9 | | 204.8 |
| C-10 | 6.43 s | 72.8 |
| C-11 | | 132.6 |
| C-12 | | 142.2 |
| C-13 | 6.05 (t,8) | 75.9 |
| C-14 | 2.14 m | 36.2 |
| C-15 | | 44.1 |
| C-16 | 1.18 s | 26.8 |
| C-17 | 1.18 s | 21 |
| C-18 | 1.94 s | 14.9 |
| C-19 | 1.67 s | 10.2 |
| C-20 | 4.23 | 72 |
| C-1' | | 173.4 |
| C-2' | 5.46 (d,7) | 75.8 |
| C-3' | 5.8 (dd 7,7) | 55 |
| N—H | 7.27 (t,7) | |
| CH$_3$(OAc) | 2.2 s | 22.2 |
| CH$_3$(OAc) | 2.4 s | 23.3 |
| Bz | 7.4–8.1 m | 126.8–138.1 |
| CO(OAc) | | 170.2 |
| CO(OAc) | | 170.2 |
| CO(OBz) | | 167.2 |
| CO(NBz) | | 171.2 |
| C-1'' | | 173.1 |
| C-2'' | 2.72 m | 30 |
| C-3'' | 2.52 m | 30 |
| C-4'' | | 173.1 |
| C-1''' | 3.58 m | 47 |
| C-2''' | 2.96 m | 51 |
| N—H | 3.58 (t,7) | |

Note that the tetrabutylammonium salt of taurine may easily be reacted with other 2'-O-acyl acid taxols, such as 2'-glutaryltaxol. 2'-glutaryltaxol can be formed easily by substituting glutaric anhydride for succinic anhydride. It is believed that other members of the oxalic acid series and other anhydrides may react with taxol more or less equivalently to the compounds specifically disclosed. Note that, in some instances, 2'-glutaryltaxol may be preferred to the use of other 2'-O-acyl acid taxols. Further, it is contemplated that the salt forming moiety may be replaced with H or another alkaline or alkaline earth metal.

EXAMPLE 3

A solution of 280 mg 3-amino-1-sulfopropionic acid in distilled water was formed, and 1 ml tetrabutylammonium hydroxide was added. The solution was stirred at 60° C. for one hour, and then evaporated to dryness. The products were dissolved in about 15 ml THF and excess 3-amino-1-sulfopropionic acid was removed by filtration. The filtrate was evaporated, and redissolved in 2 ml dried THF for subsequent reaction. A solution of 130 mg 2'-succinyltaxol and 50 μl of triethylamine in 4 ml of dry THF was formed, and the solution was cooled down to 0° C. A 50 μl aliquot of isobutylchloroformate was added to the reaction mixture, and the solution was warmed to room temperature in about 15 minutes. This was followed by the addition of 0.6 ml of 3-amino-1-sulfopropionic acid tetrabutylammonium salt in THF solution (equivalent to 108 mg of 3-amino-1-sulfopropionic acid tetrabutylammonium salt). The reaction mixture was stirred at room temperature for three hours, and reaction progress was monitored by TLC with 4/1 ethyl acetate/methanol. The reaction solution was then filtered and evaporated, with the product being purified by flash chromatography using silica gel (300 mm × 15 mm bed with a 10/1 dichloromethane/methanol eluent). A yield of 128 mg (71.2%) of the homogenous tetrabutylammonium salt of taxol resulted.

The tetrabutylammonium salt was converted to the sodium salt by placing 120 mg of 2'-{[4-((3-sulfopropyl))amino)-1,4-dioxobutyl]oxy}taxol tetrabutylammonium salt in a beaker with Dowex 50 ion exchange resin in the Na$^+$ form (approximately 3 ml of resin per 3 ml deionized water). The mixture was stirred at room temperature for about 1.5 hours, and then passed through a resin column which contained 2 ml of resin in the Na$^+$ form, and using deionized water as a solvent. The solution was azeotroped with acetonitrile and yielded 84 mg (79.3%) of 2'-{[4-((3-sulfopropyl)-amino)-1,4-dioxobutyl]oxy}taxolsodium salt:

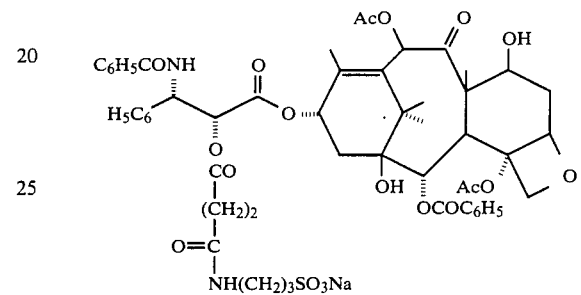

Characterization data for this compound is presented in Table 5, and NMR chemical shift data is presented in Table 6

TABLE 5

Characterization Data For
2'-{[4-((3-Sulfopropyl)Amino)-1,
4-Dioxobutyl]oxy}taxol Sodium Salt

| | |
|---|---|
| m.p. | 168–169° C. |
| $[\alpha]_D^{20}$ | −29° (0.001, MeOH) |
| IR (KBr): | 3480, 3000, 1760, 1740, 1660, 1550, 1400, 1260, 1050 cm$^{-1}$ |
| UV λ$^{MeOH\ max}$: | 279 nm (ε 974), 271 nm (ε 1240), 228 nm (ε 12719) |
| MS (FAB): | 1119 (MNa$^+$), 1097 (MH$^+$) |

TABLE 6

NMR Data For
2'-{[4-((3-Sulfopropyl)Amino)-1,
4-Dioxobutyl]oxy}taxol Sodium Salt

| Position | $^1$H Shift (ppm from TMS) Coupling (hertz) | $^{13}$C Shift (ppm from TMS) |
|---|---|---|
| C-1 | | * |
| C-2 | 5.63 (d,7) | 74.8 |
| C-3 | 3.8 (d,7) | 46 |
| C-4 | | 80.8 |
| C-5 | 4.99 (d,9) | 84.2 |
| C-6 | 2.5 m | 34.7 |
| C-7 | 4.34 m | 75.9 |
| C-8 | | 57.5 |
| C-9 | | 204.2 |
| C-10 | 6.44 s | 71.3 |
| C-11 | | 131.6 |
| C-12 | | 141.2 |
| C-13 | 6.05 (t,8) | 75.2 |
| C-14 | 2.14 m | 35.7 |
| C-15 | | 42.8 |
| C-16 | 1.16 s | 25.6 |
| C-17 | 1.16 s | 19.4 |
| C-18 | 1.93 s | 13.6 |
| C-19 | 1.67 s | 8.9 |
| C-20 | 4.21 s | 70.8 |

TABLE 6-continued

NMR Data For
2'-{[4-((3-Sulfopropyl)Amino)-1,
4-Dioxobutyl]oxy}taxol Sodium Salt

| Position | $^1$H Shift (ppm from TMS) Coupling (hertz) | $^{13}$C Shift (ppm from TMS) |
|---|---|---|
| C-1' | | 172 |
| C-2' | 5.44 (d,7) | 74.2 |
| C-3' | 5.79 (dd 7,7) | 53.6 |
| N—H | 7.25 (t,7) | |
| CH$_3$(OAc) | 2.2 s | 20.9 |
| CH$_3$(OAc) | 2.4 s | 21.6 |
| Bz | 7.4–8.1 m | 126.8–138.1 |
| CO(OAc) | | 169 |
| CO(OAc) | | 170.2 |
| CO(OBz) | | 166.4 |
| CO(NBz) | | 170.2 |
| C-1" | | 171.9 |
| C-2" | 2.75 (t,7) | 29 |
| C-3" | 2.54 (t,7) | 29.8 |
| C-4" | | 171.9 |
| C-1'" | 3.25 m | 37.9 |
| C-2'" | 1.98 m | 28.3 |
| C-3'" | 2.85 (t,7) | ** |

\* under CHCl$_3$ signal
\*\* under MeOH signal

Note, it is envisioned that sodium can be replaced with H or any other salt forming moiety such as other alkaline or alkaline earth metals, and ammonio groups.

EXAMPLE 4

A solution of 26 mg 2'-succinyltaxol and 20 μl of triethylamine in 2 ml of dried THF was prepared under argon gas atmosphere, and the solution was cooled to 1° C. A 10 μl aliquot of isobutylchloroformate was added to the solution, and the reaction mixture was warmed to room temperature in about 15 minutes. Following the warming step, 5 μl ethylene glycol were added, and the reaction mixture was stirred at room temperature for 15 hours, with the reaction progress monitored by TLC with 1:1 dichloromethane/ethyl acetate. The reaction was stopped by filtering the precipitate, and evaporating the solvent. Crude products were purified by preparative TLC (1:3 dichloromethane/ethyl acetate), yielding 25 mg (83.3%) of 2'-{[4-((2-hydroxyethyl)oxy)-1,4-dioxobutyl]oxy}taxol:

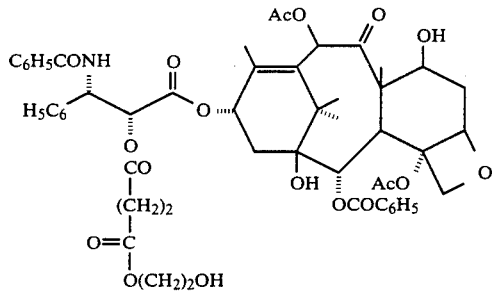

Characterization data are presented in Table 7 and NMR chemical shift data are presented in Table 8 below.

TABLE 7

Characterization Data For
2'-{[4-((2-hydroxyethyl)oxy)-1,4-dioxobutyl]oxy}taxol

| | |
|---|---|
| m.p. | 164–165° C. |
| [α]$_D^{20}$ | −32.5° (0.002, MeOH) |
| IR (KBr): | 3500, 2950, 1760, 1740, 1660, 1390, 1260, 1160, 1080, 1040 cm$^{-1}$ |

TABLE 7-continued

Characterization Data For
2'-{[4-((2-hydroxyethyl)oxy)-1,4-dioxobutyl]oxy}taxol

| | |
|---|---|
| UV λ$^{MeOH\ max}$: | 279 nm (ε 609), 272 nm (ε 831), 228 nm (ε 14404) |
| MS (FAB): | 1020 (MNa$^+$), 998 (MH$^+$) |

TABLE 8

NMR Data For
2'-{[4-((2-hydroxyethyl)oxy)-1,4-dioxobutyl]oxy}taxol

| Position | $^1$H Shift (ppm from TMS) Coupling (hertz) | $^{13}$C Shift (ppm from TMS) |
|---|---|---|
| C-1 | | 79.1 |
| C-2 | 5.7 (d,7) | 75.8 |
| C-3 | 3.8 (d,7) | 45.8 |
| C-4 | | 81 |
| C-5 | 4.95 (d,9) | 84.3 |
| C-6 | 2.56 m | 35.6 |
| C-7 | 4.43 m | 75.8 |
| C-8 | | 58.2 |
| C-9 | | 204 |
| C-10 | 6.29 s | 72.1 |
| C-11 | | 132 |
| C-12 | | 142.3 |
| C-13 | 6.23 (t,8) | 75.8 |
| C-14 | 2.42 m | 35.6 |
| C-15 | | 43.2 |
| C-16 | 1.23 s | 26.8 |
| C-17 | 1.15 s | 20.5 |
| C-18 | 1.94 s | 14.3 |
| C-19 | 1.70 s | 9.8 |
| C-20 | 4.19 (d,8) | 72.1 |
| C-1' | | 172.2 |
| C-2' | 5.48 (d,3) | 74.3 |
| C-3' | 5.97 (dd 3,9) | 52.9 |
| N—H | 7.14 (d,9) | |
| CH$_3$(OAc) | 2.25 s | 22.1 |
| CH$_3$(OAc) | 2.45 s | 22.8 |
| Bz | 7.4–8.1 m | 126.8–138.1 |
| CO(OAc) | | 168 |
| CO(OAc) | | 169.9 |
| CO(OBz) | | 167 |
| CO(NBz) | | 167.3 |
| C-1" | | 171 |
| C-2" | 2.65 m | 29 |
| C-3" | 2.78 m | 29 |
| C-4" | | 171 |
| C-1'" | 3.7 (t,7) | 66.2 |
| C-2'" | 4.1 m | 61 |

EXAMPLE 5

To a 10 ml flask, 20 mg taxol, 40 mg of dicyclohexylcarbodiimide, and 20 mg of N-carbobenzyl-γ-aminobutyric acid were added. The reactants were dissolved in 4 ml of dry acetonitrile (dry acetonitrile was obtained by passing acetonitrile through activated alumina). After stirring the reaction mixture at room temperature for 30 hours, the solution was filtered to remove precipitated dicyclohexylurea. The solvent was then removed under vacuum, and the crude products were separated by preparative TLC with 45:55 hexane/ethyl acetate. This yielded 19.1 mg (75.9%) of pure 2'-N-CBZ-γ-aminobutyryltaxol.

2'-γ-aminobutyryltaxol formate was synthesized by the addition of 6 mg of 2'-N-CBZ-γ-aminobutyryltaxol to 1.5 ml of methanol. Upon the dissolution of the CBZ-taxol derivative, 1 ml of formic acid was added to form a 40% formic acid/methanol solution. The reaction was carried out by adding 5 mg of 5% of Pd/C to the solution, and stirring it at room temperature for 26 hours. The reaction was stopped by filtering off the Pd/C, and drying the filtrate under vacuum. This yielded 2'-γ-aminobutyryltaxol formate:

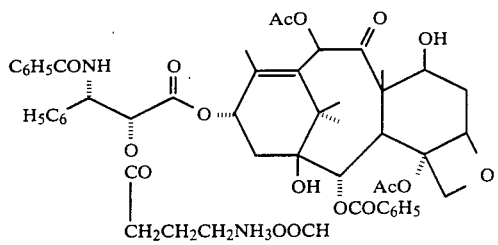

After a few hours, proton NMR and TLC with 2:1:0.02 dichloromethane/ethylacetate/methanol showed that the 2'-γ-aminobutyryltaxol formate had decomposed back to taxol.

EXAMPLE 6

Taxol's water solubility was determined by dissolving 1.6 mg of taxol in 10 ml of distilled water saturated with 1-octanol in a 60 ml separatory funnel, and 10 ml of 1-octanol saturated with distilled water was then added. The funnel was shaken, and allowed to stand for about 30 minutes until the organic and aqueous phases separated. UV absorption measurements at 228 nm were made of the aqueous layer and/or octanol layer, with the octanol layer being diluted 5 times before measurement.

Following the same procedure as above, 0.8 mg of 2'-[(3-sulfo-1-oxopropyl)oxy]taxol sodium salt, 0.8 mg of 2'-{[4-((2-sulfoethyl)amino)-1,4-dioxybutyl]oxy} taxol sodium salt and 0.7 mg of 2'-{[40((3-sulfopropyl)amino)-1,4-dioxybutyl]oxy} taxol sodium salt had their water solubilities determined relative to taxol; the results are presented below in Table 9.

TABLE 9
TAXOL DERIVATIVE WATER SOLUBILITIES RELATIVE TO TAXOL

| Compound | Relative Solubility |
| --- | --- |
| Taxol | 1 |
| 2'-[(3-sulfo-1-oxopropyl)oxy]taxol sodium salt | 210 |
| 2'-{[4-((2-sulfoethyl)amino)-1,4-dioxybutyl]oxy}taxol sodium salt | 191 |
| 2'-{[4-((3-sulfopropyl)amino)-1,4-dioxybutyl]oxy}taxol sodium salt | 118 |

Table 9 indicates that the 2'-acryloyltaxol derivative had the highest water solubility, and is 210 times more water soluble than taxol. Note that the taurine 2'-succinyltaxol derivative has a much greater water solubility than the 3-amino-1-sulfopropionic acid derivative of 2'-succinyltaxol; however, both compounds have solubilities more than 100 times greater than taxol. The decreased solubility for the 3-amino-1-sulfopropionic acid derivative of 2'-succinyltaxol is probably due to the increased alkyl chain length.

Thus, the present invention discloses new taxol derivatives with increased water solubility in comparison to underivatized taxol, and which are stable for longer periods of time than certain previous derivatives of taxol which had increased water solubilities. These compounds are produced by new processes that result in high yields of essentially pure compounds. Characterization data and NMR studies confirm the structure and properties of the taxol derivatives of the present invention. In addition to having high water solubilities and improved stability, these compounds retain their bioactivity and usefulness as antineoplastic, antileukemic and anti-cancer prodrugs.

Contemplated equivalents of the water soluble taxol derivatives of the present invention include 2'-acryloyl and 2'-O-acyl acid derivatives of taxol which have one or more side chain or ring substituents substituted with a non-interfering group (e.g., a substituted group which does not seriously alter the desirable properties of the taxol derivatives of the present invention), such as but not limited to, substitution of —H, —OH, —OR, —NR, —Ar, (aryls) or =O for another non-interfering moiety.

From the above teachings, it is apparent that many modifications and variations of the present invention are possible. It is therefore to be understood that the invention may be practiced otherwise than as specifically described.

We claim:

1. A taxol compound having the following structure:

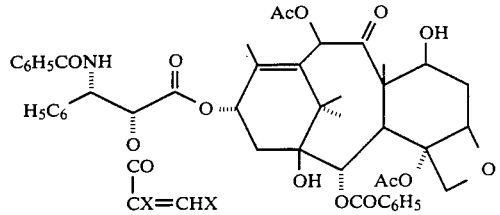

wherein:

X is selected from the group consisting of H, alkyls, and aryls.

2. A compound according to claim 1, wherein:

X is H.

3. A water soluble taxol compound having the following structure:

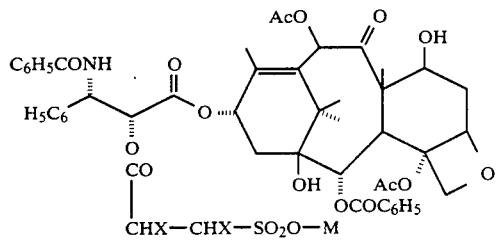

wherein:

X is selected from the group consisting of H, alkyls, and aryls; and

M is selected from the group consisting of H, alkaline metals, and ammonio groups.

4. A compound according to claim 3, wherein:

X is H, and

M is Na.

5. A water soluble taxol compound having the following structure:

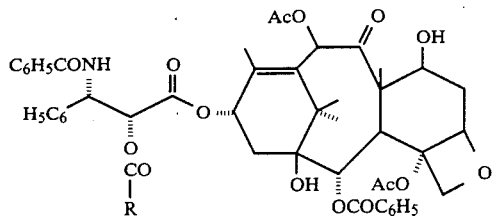

wherein:

R is selected from the group consisting of:

—(CH$_y$)$_n$—CO—NH—(CH$_2$)$_z$—SO$_2$O—M, and

—(CH$_y$)$_n$—CO—O—(CH$_2$)$_z$—OH; wherein:

M is selected from the group consisting of H, alkaline metals, and ammonio groups, n is 1 to 3, y is 1 to 2, provided y is not 1 when is 1, and z is 2 to 3.

6. A compound according to claim 5, wherein:

Y is 2, n is 2, and z is 2.

7. A compound according to claim 5, wherein:

Y is 2, n is 2, and z is 3.

8. A compound according to claim 5, wherein:

M is a quaternary ammonium.

* * * * *

UNITED STATES PATENT AND TRADEMARK OFFICE
CERTIFICATE OF CORRECTION

PATENT NO. : 5,059,699

DATED : October 22, 1991

INVENTOR(S) : David G.I. Kingston; Zhi-Yang Zhao

It is certified that error appears in the above-identified patent and that said Letters Patent is hereby corrected as shown below:

Column 2, line 3; change "including" to --inducing--.

Column 4, line 51; change "($MH^{30}$)" to --($MH^+$)--.

Column 9, line 4; change "2'-](3-sul-" to --2'-[(3-sul- --.

Column 9, line 22; change "$CH_2Cl_2MeOH$" to --$CH_2Cl_2$/MeOH--.

Column 16, line 15; change "Ar, (aryls)" to --Ar(aryls),--.

Correct the structures illustrated at the following locations to include a second methyl substituent at the C15 position:

Column 2, lines 40-51;
    Column 7, lines 38-50;
    Column 8, lines 1-14; and
    Column 10, lines 28-40.

Correct the structures illustrated at the following locations to include a single bond between the oxygen bonded to the 2' position of the side chain and the adjacent carbonyl group so that the portion of the structure reading

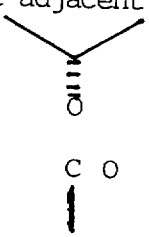    should read    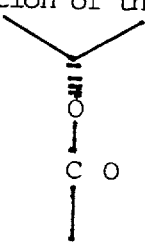

Column 10, lines 28-40;
    Column 12, lines 17-30;
    Column 13, lines 46-58;
    Column 15, lines 3-13; and

UNITED STATES PATENT AND TRADEMARK OFFICE
CERTIFICATE OF CORRECTION

PATENT NO. : 5,059,699

DATED : October 22, 1991

INVENTOR(S) : David G. I. Kingston, et. al.

It is certified that error appears in the above-identified patent and that said Letters Patent is hereby corrected as shown below:

Claims 1, 3 and 5.

Signed and Sealed this

Twenty-fifth Day of May, 1993

Attest:

MICHAEL K. KIRK

Attesting Officer

Acting Commissioner of Patents and Trademarks

UNITED STATES PATENT AND TRADEMARK OFFICE
CERTIFICATE OF CORRECTION

PATENT NO. : 5,059,699
DATED : October 22, 1991
INVENTOR(S) : David G.I. Kingston; Zhi-Yang Zhao It is certified that error appears in the above-identified patent and that said Letters Patent is hereby corrected as shown below:

Column 18, line 4; change "when is" to --when n is--.

Signed and Sealed this

Tenth Day of August, 1993

Attest:

MICHAEL K. KIRK

Attesting Officer    Acting Commissioner of Patents and Trademarks